United States Patent [19]
Elkind

[11] Patent Number: 6,149,586
[45] Date of Patent: Nov. 21, 2000

[54] SYSTEM AND METHOD FOR DIAGNOSING EXECUTIVE DYSFUNCTIONS USING VIRTUAL REALITY AND COMPUTER SIMULATION

[76] Inventor: Jim Elkind, 76 Cotton St., Newton, Mass. 02158

[21] Appl. No.: 09/239,284

[22] Filed: Jan. 29, 1999

Related U.S. Application Data

[60] Provisional application No. 60/072,992, Jan. 29, 1998.
[51] Int. Cl.[7] ........................................... A61B 5/00
[52] U.S. Cl. .................... 600/300; 600/301; 128/897; 434/236
[58] Field of Search .......................... 600/300; 345/419; 434/29, 219, 236, 433; 128/897

[56] References Cited

U.S. PATENT DOCUMENTS

| | | | |
|---|---|---|---|
| 4,086,710 | 5/1978 | Craine | 434/236 |
| 5,736,986 | 4/1998 | Sever, Jr. | 345/419 |
| 5,782,639 | 7/1998 | Beal | 434/29 |
| 5,807,114 | 9/1998 | Hodges et al. | 434/236 |

*Primary Examiner*—Cary O'Connor
*Assistant Examiner*—Michael Astorino
*Attorney, Agent, or Firm*—David D. Lowry Brown, Rudnick, Freed & Gesmer, P.C.

[57] ABSTRACT

The present invention includes using computer simulation and virtual reality (VR) tests for determining categories of neuropsychological dysfunctions, including executive dysfunctions. A test subject interacts with a computer generated simulated environment according to a predetermined test script. The test script presents a simulated environment of sight and sound which can closely mirror a real activity, such as daily routines performed by everyone; or an environment such as a game played by the subject. The test script is designed to present situations where subjects with executive dysfunctions will interact and make decisions which indicate the dysfunctions. During the testing, other physiological measurements may be measured and recorded, including subject respiration, heart rate, blood pressure, skin changes etc. The results of the testing are interpreted by scoring the subject's reactions, and provide an indication of the subject's dysfunctioning. These results may be used along with other standardized tests as known in the art, to produce a complete prognosis.

15 Claims, 2 Drawing Sheets

continued

SYSTEM AND METHOD FOR DIAGNOSING EXECUTIVE DYSFUNCTIONS USING VIRTUAL REALITY AND COMPUTER SIMULATION

RELATED APPLICATION

The present application claims the benefit of U.S. Provisional Application No. 60/072,992 filed on Jan. 29, 1998, which is incorporated herein by reference.

BACKGROUND

Continuing medical and tehnological advances have resulted in more prematurely born infants living than ever before, and current research has shown that 25% of those infants carry mild to moderate disabilities. In addition, there are large numbers of young adults who suffer brain damage and cognitive dysfunctions caused by head injuries. It is estimated that more than seven million children between the ages of six and twenty-one, and approximately twenty million adults over twenty-one have either mental retardation, learning disabilities, or traumatic brain injuries with attendant cognitive deficits. One category of cognitive deficits are known as executive dysfunctioning.

Executive Functions are those functions which significantly determine the extent to which a person exhibits appropriate and responsible adult behavior. They enable individuals establish priorities, make decisions, or alter a course of action when intervening circumstances require action modifications. Of the cognitive defects that impact daily functioning of people with neurological deficits, executive functions effect the everyday personal, interpersonal, and work related behaviors in ways that critically impact interpersonal relationships and functional abilities in the areas of independent living and work.

Four major components of executive functioning are volition, planning, purposeful behavior and effective performance.

Volition is will, agency, choice that emanates from knowing what one wants and contains the motivation to gratify them.

Planning reflects one's ability to plan and execute a sequential series of goal directed behaviors. Competent planning demonstrates skills in organizing, thoughts and plans, securing and working with the necessary people, equipment, tools, etc. Effective planning also requires mental flexibility when unexpected obstacles intervene.

Purposeful behavior reflects the ability to initiate purposeful sequentially executed behaviors that demonstrate awareness of self, others, and the environment. It involves the person's capacity to employ flexibility when circumstances require modifications in goal and adoption plans.

Effective performance indicates the capacity to observe, correct, and regulate one's own behavior, affect speed of operation, and thoroughness of: performance. Attitude and judgment or performance thoroughness are important to observe and assess. (Lezak, 1995, PP 650–677)

Disorders of executive functioning can be reflected by inadequate self care skills, difficulty, managing or spending money wisely, and problems initiating and completing intentional, goal-directed, self monitoring actions, There usually is evidence of all or some of the following deficiencies:

1. Problems with volition and initiating behavior can be reflected by a lack of motivation, the inability to initiate and intentional action, and may involve difficulties in executing and sustaining focused, goal-directed actions. There often is a lack of self awareness and sensitivity towards others.

Example 1: A person is aware of the need to shower. brush teeth, comb hair, and wear clean clothes, but is unable to do this regularly unless another person remains present and directs each step of the morning hygiene and personal care routine.

Example 2: A man's inability to stop flooding every new girl friend with gifts, invitations, and phone calls results in his inevitably losing every newly initiated relationship. The man always experiences sorrow and remorse for causing the woman enough distress to break-up with him. However, regardless of the guidance or reminders of behavioral rules, the man can not refrain from resorting to the same behaviors when starting out with a new girlfriend.

2. Planning deficits are often related to poorly organized action sequences that include the necessary people and resources to reach the intended goal. The insufficient awareness of the relationship between planning, actions and outcome poses problems when these individuals are confronted with the unanticipated repercussions of their poor planning and inability to implement alternative strategies.

Example 3: A woman wants to complete her college education. She registers for courses that are too demanding and beyond her academic skills. She is unable to attend classes, maintain a part time employment, and she refuses any advice and suggestions from college counselors or professionals. Their recommendation that fewer and less demanding courses be considered is ignored and the woman drops out of school, blaming her failures on the teachers and "system."

Example 4: A person wants to live in his own apartment and "run his own life." However, he makes no attempt to earn a steady job which would enable him to afford an apartment and the self maintenance expenses. While he sees the relationship between wanting an apartment, needing the money to pay rent, and getting a regular paying job, he makes no independent attempt to look for a job or contact a vocational rehabilitation agency.

3. Inability to execute, purposeful behaviors is characteristically reflected in impulsive actions, disinhibited speech and/or conduct where the person is unable to contain irrelevant or reflexive responses. Difficulties also occur when routinely executed functions no longer are appropriate and the person cannot modify his plan or behavior according to those changes (Levinson, 1996).

Example 5: A young clerical employee talks with his financial tutor about taking a week's vacation to Disney World. He wants to travel by airplane, stay in a hotel, and visit the park. Discussions reveal neither an awareness of the planning process, nor a realistic idea of the involved costs. His desire to contact airlines, hotels, and the park without assistance were initially respected. A lack of results led to the counselor and the employee into developing a written money saving and planning process. With frequent case-manager visits, he was able to follow the written directions.

4. Ineffective performance refers to the difficulty a person has observing, modifying and regulating his/her behavior.

Example 6: A man with average intelligence receives financial counseling regarding budgeting, bill paying, managing his check book, and use of funds for leisure activities and life essentials. Despite agreed upon strategies and guidelines cuing geared to help the person live within his financial boundaries, he usually cashes pay checks immediately and spends seventy-five percent of his earnings despite bills, obligations, and other expenses which require attention.

5. Perseverations are behaviors or verbalizations which, driven by internal, unconscious and/or neurological determinants, continue well beyond interpersonal and/or circumstantial appropriateness.

Example 7: A person with cognitive disabilities is taught how to greet guests who come to the door. However, once he introduces himself, asks the person's name, and says "pleased to meet you." he persists in going through the script long after it is applicable. (This behavior also may reflect impulsivity.)

6. Impulsive behaviors are those that occur without regard to contextual or social appropriateness without regard for consequences.

Example 8: A person living from a fixed income and budget goes food shopping. He brings his shopping list and the usual amount of money. While selecting items from this list he is approached by a promoter to purchase a manual food processor on a ten day, fully refundable trial. The person makes the purchase, is unable to complete the necessary food purchases and blames the independent living instructor for not having him bring sufficient funds. (ALSO, inadequate planning and self monitoring may also operate.)

7. Diminished self and interpersonal awareness exists when a person is unaware of how his/her behavior impacts another person, is (in)appropriate to the Context. and demonstrates little self awareness as well as reduced capacity to alter behavior or acknowledge it.

Example 9: A person applies for and interviews for a job. During the meeting, the applicant admonishes the interviewer for being late. When job duties are described the applicant complains that there is too much time required filling in as a receptionist. When the applicant did not notice the interviewer check and re-check his watch, cross his arms, and interrupt the applicant mid sentence when the applicant scorned the salary. Later when asked how the interview proceeded, the candidate disclaimed any interest in the job, saying that the salary and hours weren't worth it.

As these examples show, a person with executive dysfunction may outwardly appear to function with normal skills, but have dysfunctions which manifest during everyday routines. Diagnosing these dysfunctions is problematic for the very reason that they are often not observable from a typical lab testing situation. A person may function perfectly during analysis and review of activities. It is only when they are engaged in daily activities that these dysfunctions appear.

Attempting to determine executive dysfunctions from observing the person during daily situations is problematic. First, there is the time and expense of accompanying and observing the person during their daily routines. Such observation may take several days or weeks to readily determine a pattern of executive dsyfunctions. Further, the presence of the observer can affect the results, wherein the person will modify their behavior or take different actions because they know the observer is there. For dysfunctional persons attempting to autonomously function in the real world, the presence of an observer is a self-conscious reminder to behave "correctly", as well as a support as a person the dysfunctional individual can defer to for advice instead of making their own decisions.

SUMMARY

The present invention includes a system and method for testing a subject for determining neuropsychological dysfunctions, including executive dysfunctions, using computer simulated reality to provide more accurate assessments of a subject's executive deficits. The illustrative embodiment of the present invention includes a predetermined test scenario script, to provide a test scenario to the subject. A scenario simulation component on the computer, produces a simulated reality environment based on said predetermined test scenario script, which is displayed to the subject using visual systems such as monitors and head mounted displays (HMDs).

The subject interacts and responds to the environment by various input devices including keyboards, joysticks, pointing devices, tactile and sensory gloves, etc. A test scenario result reviewing component, accepts the input from the subject in response to the subject interacting with the simulated reality environment, and determines result information based on analyzing said subject's interactions. The result information includes processing by standard techniques including statistical analysis, to determine a score.

The system also accepts as input physiological measurements from said subject.

The scenarios provide more ecologically valid scenes that simulate real life situations, and will identify and predict, with greater applicability to real life, validity and reliability, executive functioning disabilities and their likely impact on daily living activities. Dysfunctions such as difficulties in correctly identifying categories of sorting, preservative responses, inability to shift concepts/sets are analyzed and identified to determine the existence and significance of any deficits in executive functioning.

Advantages of the present invention include an objective, repeatable test standard for gauging individuals and measuring results. Computer simulations allow standardized tests to be presented to individuals, allowing comparison of results. The results are more valid and reliable than existing paper and pencil tests that are administered by different examiners, and scored by different interpreters. The results demonstrate repeatedly the nature and extent of the cognitive disabilities, and the results translate, because of their ecological validity, more easily into rehabilitation training (whether by VR "sessions" or other methods) and transfer into real world environments. Further, a fully developed test scenario is low in cost to administer. Actors and props are not necessary to enact situations for observing a test subject's reactions.

Another advantage of the present invention is a "safe" environment for test subjects to interact in real-world situations without harm or loss of money. Test parameters such as background noise can be readily adjusted to requirements for the test subject. Further, since the test subject is typically limited in the movement they can perform during the test, it is easy to monitor the test subject including physiological measurement instruments such as blood pressure, EEG, EKG, galvanic skin sensors, eye and/or hand movement.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1:
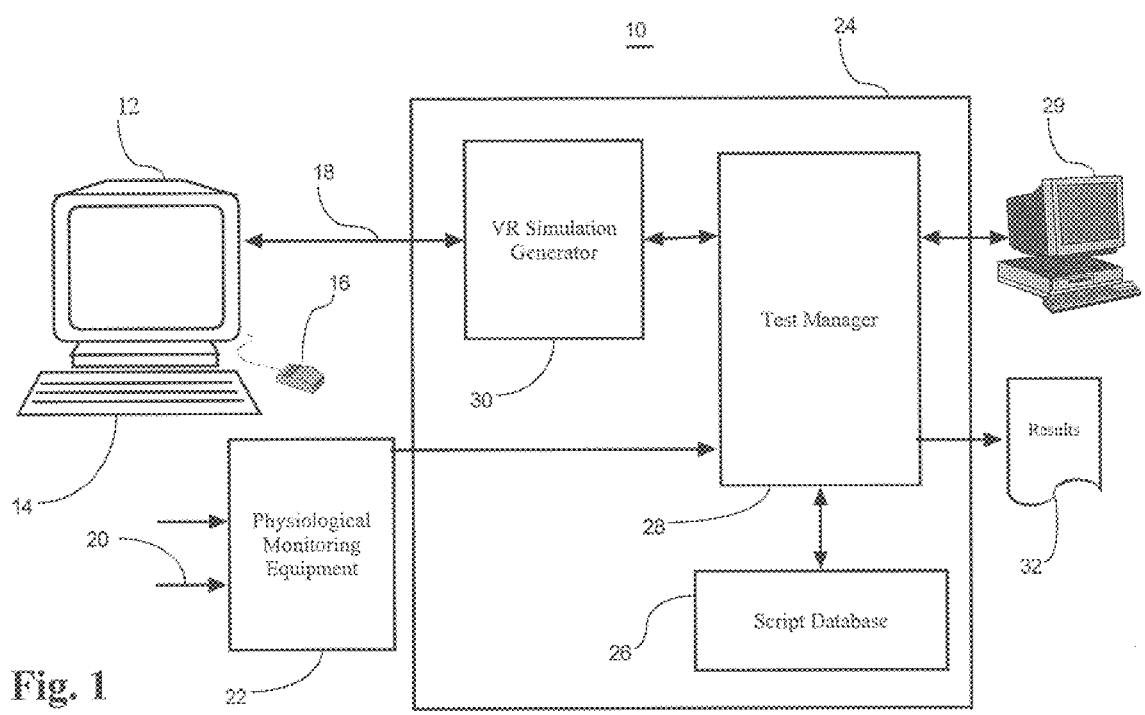
FIG. 1 is a block diagram showing the major components of an illustrative testing system according to the present invention.

The present invention includes using computer simulation and virtual reality tests for determining categories of neuropsychological dysfunctions, including executive dsyfunctions. An example system 10 according to the present invention is shown in FIG. 1. A test subject views a display monitor 12 which displays the simulation according to the scenario. Sounds from speakers can also be provided (not shown). The subject interacts with the system by input devices including keyboard 14 and mouse 16. Scenarios for such a system are developed for use on a standard, desk top computer 24 and monitor 12, for example. Such equipment will not eliminate awareness of and sensitivity to the surrounding environment; but wraparound monitors 12 most likely can increase sense of immersion and exclude greater amounts of the immediate environment. Another feature is that subjects benefit from real time graphics, i.e. actions of the subject/player will be immediately responded to on the monitor 12.

Of course, to provide a much more immersive environment, the present invention includes using displays, sound systems and input devices which create a full environment for the subject to interact within. Immersive Virtual Reality Scenarios are those in which the subject feels as if they are actually in the environment to the extent that they may temporarily suspend their awareness of and sensitivity to, the surrounding environment. The total immersion in a visual representation of a simulated reality, over time enables the person to interact with it as if it were real. Such displays may include surrounding rooms and head mounted displays (HMD).

An example surrounding room with projections, is the Visiondome®, available from Alternate Realities Corporation of Durham, N.C. A subject is surrounded by a spherical dome typically 4–7 meters in diameter, with displays covering a full 180 degrees. Also available are stereoscopic displays which allow actual three dimension viewing of environments. ImmersaDesk Pyramid Systems of Southfield Mich., offers the ImmersaDesk, a "drafting-table format prototype device. Using stereo LCD shutter glasses and magnetic head/hand tracking, this projection-based system offers a type of virtual reality that is extremely immersive and offers high-resolution color-correct "stereoscopic displays".

Head Mounted Displays (HMD) are usually helmets in which optical equipment is built in. The extent to which haptic capacity may be available would be determined by the sophistication of the HMD. There are at least 30 different manufacturers of HMD's ranging in cost from a few hundred dollars to thousands. Example HMDs are the Glasstron Model PLM- A55 available from Sony Corporation, or the V6 head mounted display available from Virtual Reality Source of Arvada, Colo.

Input devices include buttons, joysticks, mice, touch screens, touch pads, voice command recognition systems, eye movement and blink detectors, head movement detectors, and sensory and haptic gloves such as the Cyberglove® and the CyberTouch system, both produced by Virtual Technologies Incorporated and available from Virtual Reality Source of Arvada, Colo. Haptic gloves not only record a subjects movements and gestures, but also provides tactile feedback and object movement thus facilitating to a greater degree, a sense of playing the game in the actual setting or environment. Other input devices include hand gesturing input systems and head movement detection devices.

Other inputs from the subject can be monitored as shown by arrow 20 and physiological monitoring equipment 22. These include measurements and changes in respiration, heart rate, blood pressure (Hoter Monitor), skin perspiration measurements, etc. In addition, head and hand trackers are available, for example Polhemus Corporation of Colchester, Vt. The data is processed by appropriate physiological equipment 22 and input into the system.

The system 10 can use any general purpose computer 24, such as an Intel-based personal computer. A script database 26 stores and makes available predetermined scripts which describe and create the test environments and scenarios. A test manager component 28 processes these predetermined scripts and works in conjunction with a VR (Virtual Reality) simulation generator 30 (e.g. InterAct or Silicon Graphics system) to present the test on the display system 12, as shown by arrow 18. The test manager component 28 responds to the subject actions, to cause changes in the environment through interaction with the VR Simulation generator 30. The test manager component 28 can also accept the physiological measurements from the physiological monitoring equipment 32.

A test administrator can supervise the testing procedure through a separate monitor 29, which may be a separate computer, or a monitor connected to the system 24 by direct cable or network. The test administrator can monitor the testing procedure if desired, or simply run automated testing.

The test manager component 28 records user input and physiological measurements and interprets the results, which are then output to the test administrator's monitor 29, or printed or sent as output as shown by results 32. The predetermined script database 26 can store the test responses for each subject as well as the analysis of the responses in results. The predetermined script database 26 can be stored by any means including flash memory, local or networked disk drives, optical or magneto-optical disks and tapes.

Figure 2:
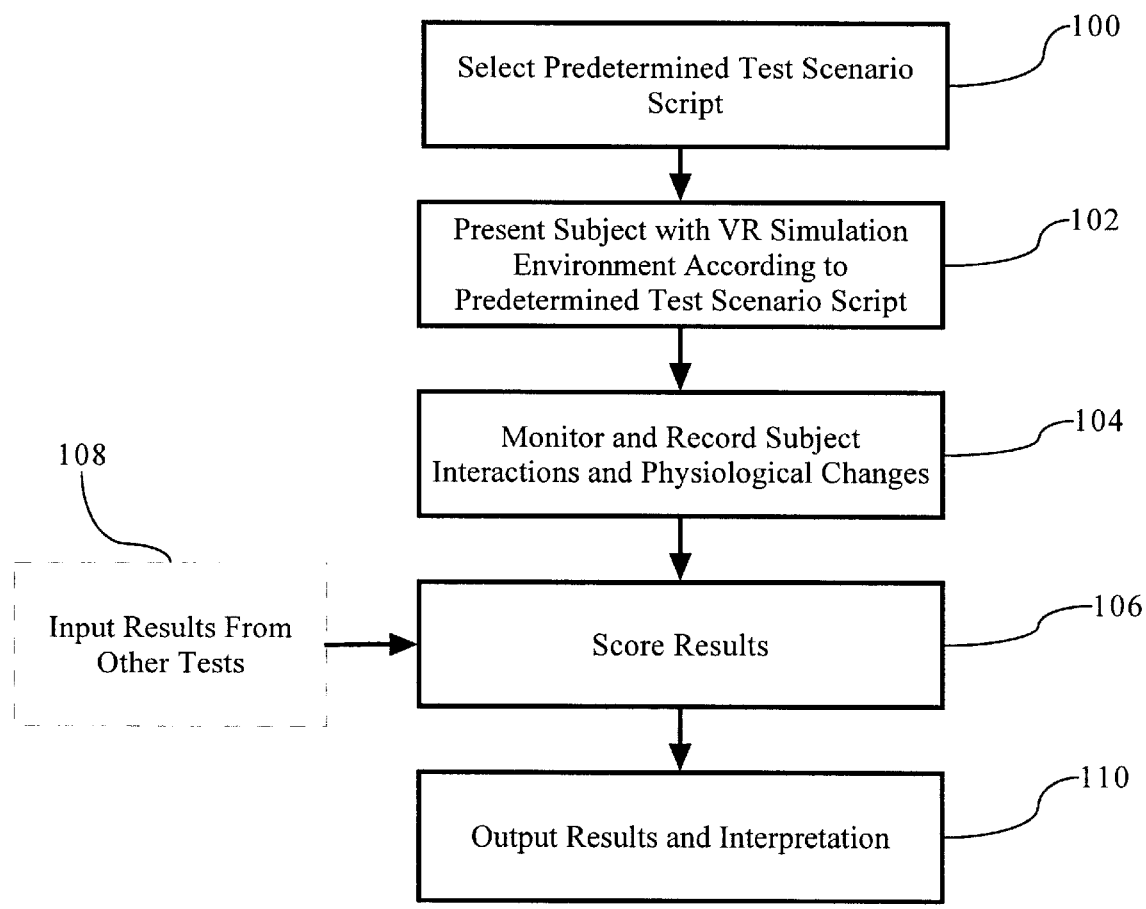
FIG. 2 is a flow chart of the steps performed according to the illustrative testing system of FIG. 1.

The steps performed by the illustrative embodiment are shown in FIG. 2. First a predetermined script to test the subject is selected, step 100. This selection may be made based on the results of previously performed tests on the subject, including standardized test, as will be described below. The subject is presented with the VR simulation in accordance with the predetermined script, step 102. As the subject reacts and interacts with the simulation, the subject's responses are recorded, step 104. If physiological measurements are also being monitored, they are recorded also.

Once the scenario is complete, the system scores the results, step 106. If other previous tests have been performed on the subject, they may be included in the scoring, as shown by 108. Finally the results and interpretations are output, step 110. The results can be in a form of statistical analysis, probability distribution, conclusion based on historical data or algorithms, and also recommended further tests or treatment.

An illustrative predetermined script presenting a test scenario will now be described. The script presents a computer card game called "Look for a Match" (LFAM). LFAM is designed to:

1. Assess a subject's capacity to form abstract concepts.
2. Assess a subject's capacity to maintain as well as shift from one principle to another.
3. Assess a subject's mental flexibility, including capacity to form abstract concepts and shift from one mental set to another with and without distractions.

The Immersive virtual reality and desktop scene is a gambling casino (for adults) and carnival for teenagers. The subject enters the casino/carnival and is invited to play "LFAM". The dealer will lay out four stimulus cards: the first will represent money items, the second, illustrate an object found in the community, third will illustrate a mode of transportation, and the fourth will illustrate a personal item found in one's home. (There are two piles of 64 cards each and the player is to place each one according to the dealer's directions or until the dealer stops the game.)

There is the background sound of muffled conversation, some additional, occupied gambling tables are pictured in the background. Upon entering the casino (carnival) the subject is immediately greeted by the dealer (barker), who speaks according to the following script.

"Hello. How are you? Please come to my table and play Let's Find A Match (LFAM). It's a lot of fun, and you look like someone who will do well and enjoy it. In this game, though, I only can indicate a correct or incorrect choice. I cannot answer any questions or provide additional information once I give the directions.

"Here are the instructions. I will lay out four cards, face up. Then you will be given a pile of cards, face down. Please take only the top card and place it below the one facing up that you think it matches. Once you place it. it cannot be removed. Then. select the next card and so on. Please do not shuffle or rearrange the cards in any way. Take your time and enjoy the game. Speed is not counted for or against you.

"If you're ready, I'll place four cards down and then you can start playing." (The dealer shows the subject the deck from which he is to draw each card, and a duplicate deck is placed to the side for possible later use.) "All right? Let's play!"

Dealing the target cards:
1. The dealer turns up one card from each category. He puts the first card on the player's far left, with the picture up and presented so it appears as it would have had the player actually turned it over. The card's background is white and it has in its center one green five dollar bill.
2. The second white card is placed immediately to the right of the first card facing the player. The card has two red supermarkets printed on it and they are centered on the white card.
3. The third white card is placed immediately to the player's right of the second card facing the player. This card has three yellow propeller planes with each one placed at the corner of an invisible, though centered, triangle. The card faces the player.
4. The fourth white card is placed immediately to the right of the third, faces up, and has on it four purple refrigerators with one located in each corner of the card.

The play is as follows:
A. Once the dealer has laid out each target card, the player places each one under the target card where he/she thinks it belongs. The subject begins to play, and the dealer indicates whether the choice is correct or incorrect by ringing a bell. If the selection is incorrect, the dealer sounds a dull gong.
B. The first category is color. After ten correct placements in a row, the dealer shifts sets and indicate right or wrong by ringing the appropriate bell. Type of object is the second category, with number of objects on a card being the third. Then the sets shift back to color, type of object. and then number.
C. In both piles the cards are arranged so that they are turned over in the following order:

1. 1 red five dollar bill
2. 4 red propeller planes
3. 2 purple $.5 bills
4. 1 red refrigerator
5. 4 green supermarkets
6. 1 yellow propeller plane
7. 4 purple $5 bills
8. 3 red refrigerators
9. 4 green propeller planes
10. 2 yellow refrigerators
11. 1 purple supermarket
12. 3 red $5 bills
13. 2 purple airplanes
14. 1 yellow supermarket
15. 3 green $5 bills
16. 4 purple refrigerators
17. 2 red supermarkets
18. 3 yellow refrigerators
19. 4 red $5 bills
20. 1 yellow refrigerators
21. 2 purple supermarkets
22. 3 green propeller planes
23. 2 yellow supermarkets
24. 3 purple $5 bills
25. 4 red supermarkets
26. 2 yellow $5 bills
27. 3 purple propeller planes
28. 4 red refrigerators
29. 2 green supermarkets
30. 1 red propeller plane
31. 4 green refrigerators
32. 1 red supermarket
33. 3 purple refrigerators
34. 4 yellow propeller planes
35. 1 green supermarket
36. 4 yellow $5 bills
37. 2 purple refrigerators
38. 3 yellow supermarkets
39. 1 green refrigerator
40. 4 purple propeller planes
41. 1 red $5 bill
42. 3 purple supermarkets
43. 4 yellow refrigerators
44. 2 green $5 bills
45. 3 red supermarkets
46. 2 yellow propeller planes
47. 1 purple refrigerator
48. 3 yellow $5 bills
49. 2 green propeller planes
50. 4 yellow supermarkets
51. 1 purple $5 bill
52. 3 green supermarkets
53. 2 red refrigerators
54. 4 green $5 bills
55. 1 purple propeller plane
56. 3 green refrigerators
57. 2 red propeller planes
58. 1 yellow $5 bill
59. 3 red propeller planes
60. 2 green refrigerators
61. 4 purple supermarkets
62. 3 yellow propeller planes
63. 2 red $5 bills
64. 1 green propeller plane C. When the "player" has made six runs of ten correct choices he is asked if he understands the principle of the game.

D. If the player exhausts his supply of cards prior to making six sets of ten correct choices, the second pack of cards is called into play.

E. However, if the player misplaces 30–40 cards in a row, than it is likely the player is unlikely to grasp the task.

F. If the player makes four correct runs, not withstanding the one or two attempts to match when the set changes, the dealer asks if the player knows the principle behind the game:

G. At card 32, a group of people walk by, with their conversation becoming louder as they get closer to the player. (This lasts through cards 32, 33, and 34.)

H. At card 42, the music begins to play with increasing loudness, reaching its highest volume at card 44. The sound diminishes over cards 45, 46, and 47.

I. At card 54, a couple passes by, stops next to the player, begins to chat and compliments him/her at how well he/she is doing. They leave by card 56.

J. (If the player is continuing) at card 72 a group of loud talking and laughing guests walk by complete their pass by card 76.

K. At card 90 the lights dim because of a power surge, but the cards still can be seen. At card 93 the lights begin to return to their full brightness which is reached at card 96.

The LFAM script is scored as follows. The subject's responses are recorded by computerized recording by the test manager 28, which notes the correctness/incorrectness of each response. Identical features on the stimulus and response card are noted. (If color and number are the same, these two features are noted electronically.) Perseverative responses are noted. (In the WCST (Wisconsin Card Sorting Test, as produced by Robert Eaton), these were the most useful diagnostic indicators of frontal lobe deficit.) Perseverative responses to the initial, color match are evidenced by persistently making an unambiguously incorrect response, i.e. Form or number, but not both.

Beyond the initial match of color, perseverative responses are those singular and unambiguous responses made in accordance to the previous set once the feature has been changed—(i.e. continuing with color, when the set has shifted to type of object, or to number). A "perseverative response exists" score begins with the first clear incorrect response is made, a second, but different incorrect set is selected, and the third incorrect selection matches the first incorrect one. (i.e. The second incorrect response of three is different from the first and third which are identical and bracket the second). If the subject selects a category which is incorrect, the perseverative score begins with the first clear incorrect salaried response. (E.g. If the correct response is color, then the perseverative response must be repetitive numerical responses or repetitive/uninterrupted form responses. If three consecutive choices are made of an incorrect principle in a trial where there is a shift from correct to incorrect response, and then another shift to a category other than that which was previously chosen, it is a perseverative response.

Perseverative errors are those continuing responses which also are errors and are indicated as such. Scoring perseverations according to the illustrative embodiment includes recognizing that a perseveration is when the subject responds according to a previously correct rule or principle. Thus there must be a "Perseverative Principle" in order to score a perseveration. The most common way to derive a Perseverative Principle is when the rule shifts. At that time, the previously correct, but no longer appropriate rule is defined as the Perseverative Principle. An unambiguous (i.e. only matches one category) response that matches the previously correct is scored as a perseveration. As an example, the subject has been correctly matches COLOR, and the rule shifts to FORM. If the subject makes a response that matches COLOR only, it is scored as a perseveration.

A perseveration may occur prior to the first correct series of 10 correct responses. If the subject makes an unambiguous incorrect response, while the response is not scored as a perseveration, that category becomes the Perseverative Principle. If the subject then makes another unambiguous response to that category, it is scored as a perseveration.

The Perseverative Principle can change. If the subject makes three unambiguous incorrect responses in a row, then that category becomes the new Perseverative Principle, and the second and third responses are scored as perseverations.

The scoring rules are as follows. Any unambiguous response that matches the Perseverative Principle is scored as a perseveration. Also, an ambiguous response that includes the previously correct rule may be scored as a perseveration, but only if it is bracketed by clear cut perseverative responses. That is, if the subject (1) makes a perseverative response, then (2) an ambiguous response, if (3) the next response is also a perseveration, then the ambiguous response (2) is also scored as a perseveration. However, if the next response (3) is not a perseveration, then the ambiguous response is not scored as a perseveration. Also, Non perseverative error scores involve subtracting the total perseverative error scores from the total score on the test.

This scenario script and test results can be analyzed along with and in deference to other standard tests which help provide a full picture of a subject's functioning and deficits. Examples of other tests include the Motion History Questionnaire (Kennedy, R. S. & McCauley, M. E. 1984), a Simulator Sickness Questionnaire (Kennedy, R. S. & Lande, N. E. et al. 1993). These tests are administered to determine to what extent each individual has experienced and continues to be sensitive to motion. Such sensitivity are important to know and note vis-a-vis responses to desk top and immersive virtual reality environments.

Another helpful standard test is the Behavioral Assessment of the Dysexecutive Syndrome [BADS], (Wilson, Barbara A., et el. 1998), which, as a more ecologically valid, yet conventional test, more specifically measures the nature and extent the syndrome of deficits in executive functioning. Also, the Vineland Adaptive Behavioral Scale addresses the degree to which a subject displays age appropriate adaptive skills; and may be helpful for interpreting overall results when combined with the present invention.

The present invention runs on any general purpose computer, including personal computers, workstations and graphics intensive drivers. The scripts are coded in any computer language, including Lisp, C, C++, Java or specially designed graphics or scripting languages. The scripts and components can be stored in any standard database, including object-oriented databases and knowledge bases. Input from the physiological monitoring equipment may be preprocessed by techniques including preamplifiers, A/D (analog to digital) converters, VCO (voltage controlled oscillators), signal processing including DSP (digital signal processing), and compression and expansion algorithms. The input may be entered by communication ports, network connections, or specially created data signal inputs into the computer system.

Although the invention has been shown and described with respect to illustrative embodiments thereof, various other changes, omissions and additions in the form and detail thereof may be made therein without departing from the spirit and scope of the invention.

What is claimed is:

1. A computer system for testing a subject for neuropsychological dysfunctions comprising:
    a predetermined test scenario script, to provide a test scenario to said subject;
    a scenario simulation component, to produce a simulated reality environment based on said predetermined test scenario script; and
    a test scenario result reviewing component, to accept input from said subject in response to said subject interacting with said simulated reality environment; and to determine result information based on analyzing said subject interacting with said simulated reality environment, including indications of perseverations by said subject while interacting with said simulated reality environment.

2. The system of claim 1 wherein said neuropsychological dysfunctions include executive dysfunctions.

3. The system of claim 2 wherein said predetermined test scenario script includes simulated reality environments which present situations with opportunities for said subject to exhibit dysfunctional behavior.

4. The system of claim 1 wherein said test scenario results reviewing component also accepts as input physiological measurements from said subject.

5. The system of claim 4 wherein said physiological measurements selected from the group include measurements of respiration, heart rate, blood pressure, and galvanic skin changes.

6. The system of claim 1 wherein simulated reality environment is provided to said subject using a head mounted display.

7. The system of claim 1 further including:
    said predetermined test scenario script includes a first rule for matching categories by said subject while interacting with said simulated reality environment, and a second rule for matching categories, which replaces said first rule for matching categories after a predetermined interval; and
    said test scenario result reviewing component notes whether said subject continues to interact with said simulated reality environment according to said first rule for matching categories.

8. A method for testing a subject for neuropsychological dysfunctions comprising:
    providing a predetermined test scenario script, said predetermined test scenario script including tests for perseverations by said subject;
    producing a computer generated simulated reality environment for said subject, said computer generated simulated reality environment based on said predetermined test scenario script;
    accepting and recording user interaction with said computer generated simulated reality environment by said subject; and
    providing an indication of neuropsychological dysfunctions based on said recording of user interaction.

9. The method of claim 8, wherein said neuropsychological dysfunctions include executive dysfunctions.

10. The method of claim 8, wherein said predetermined test scenario script includes simulated reality environments which present situations with opportunities for said subject to exhibit dysfunctional behavior.

11. The method of claim 8, wherein said step of accepting and recording user interaction with said computer generated simulated reality environment by said subject further includes:
    accepting and recording physiological measurements of said subject as said subject interacts with said computer generated simulated reality environment.

12. The method of claim 11, wherein said step of providing an indication of neuropsychological dysfunctions based on said recording of user interaction further includes:
    providing said indication of neuropsychological dysfunctions is also based on said recording of physiological measurements.

13. The method of claim 11, wherein said physiological measurements selected from the group include measurements of respiration, heart rate, blood pressure, and galvanic skin changes.

14. The method of claim 8, wherein said step of producing a computer generated simulated reality environment for said subject includes providing said subject with a head mounted display for viewing said computer generated simulated reality environment.

15. The method of claim 8, wherein said predetermined test scenario script tests for perseverations by said subject by:
    presenting said subject with a first rule for matching categories while said subject is interacting with said computer generated simulated reality environment;
    after said subject has interacted with said computer generated simulated reality environment for a predetermined interval, changing to a second rule for matching categories; and
    noting if said subject continues to interact with said computer generated simulated reality environment according to said first rule for matching categories.

* * * * *

UNITED STATES PATENT AND TRADEMARK OFFICE
CERTIFICATE OF CORRECTION

PATENT NO. : 6,149,586
DATED : November 21, 2000
INVENTOR(S) : James Elkind

It is certified that error appears in the above-identified patent and that said Letters Patent are hereby corrected as shown below:

In Claim 5, move the words "selected from the group" from after the first occurrence of the word "measurements" to after the second occurrence of the word "measurements"

In Claim 13, move the words "selected from the group" from after the first occurrence of the word "measurements" to after the second occurrence of the word "measurements"

Signed and Sealed this

Eighth Day of May, 2001

Attest:

NICHOLAS P. GODICI

Attesting Officer

Acting Director of the United States Patent and Trademark Office